United States Patent [19]

Rondeau et al.

[11] Patent Number: 5,919,273

[45] Date of Patent: *Jul. 6, 1999

[54] COMPOSITIONS AND PROCESSES FOR DYEING KERATIN FIBERS WITH AN OXIDATION BASE, A COUPLER, A CATIONIC DIRECT DYE, AND AN OXIDIZING AGENT

[75] Inventors: Christine Rondeau, Sartrouville; Jean Cotteret, Verneuil Sur Seine; Roland de la Mettrie, le Vesinet, all of France

[73] Assignee: L'Oreal, Paris, France

[*] Notice: This patent is subject to a terminal disclaimer.

[21] Appl. No.: 08/994,127

[22] Filed: Dec. 19, 1997

[30] Foreign Application Priority Data

Dec. 23, 1996 [FR] France .................................. 96 15892

[51] Int. Cl.⁶ ...................................................... A61K 7/13
[52] U.S. Cl. .......................... 8/412; 8/407; 8/408; 8/409; 8/410; 8/423; 8/426
[58] Field of Search ................................. 8/405, 406, 407, 8/408, 409, 410, 412, 421, 423, 426

[56] References Cited

U.S. PATENT DOCUMENTS

| 3,524,842 | 8/1970 | Grossman et al. | 8/426 |
| 3,578,386 | 5/1971 | Kalopissis et al. | 8/426 |
| 3,869,454 | 3/1975 | Lang et al. | 534/778 |
| 3,985,499 | 10/1976 | Lang et al. | 8/426 |
| 4,025,301 | 5/1977 | Lang et al. | 8/426 |
| 4,425,132 | 1/1984 | Grollier et al. | 8/405 |
| 5,637,115 | 6/1997 | Balzer et al. | 8/407 |
| 5,733,343 | 3/1998 | Mockli et al. | 8/426 |

FOREIGN PATENT DOCUMENTS 0 739 622  10/1996  European Pat. Off. .

*Primary Examiner*—Paul Lieberman
*Assistant Examiner*—Caroline D. Liott
*Attorney, Agent, or Firm*—Finnegan, Henderson, Farabow, Garrett & Dunner, L.L.P.

[57] ABSTRACT

A ready-to-use composition for the oxidation dyeing of keratin fibers, in particular human keratin fibers such as hair, comprising at least one oxidation base in combination with at least one coupler of substituted meta-aminophenol type, at least one cationic direct dye and at least one oxidizing agent, as well as to the dyeing process using this composition.

43 Claims, No Drawings

COMPOSITIONS AND PROCESSES FOR DYEING KERATIN FIBERS WITH AN OXIDATION BASE, A COUPLER, A CATIONIC DIRECT DYE, AND AN OXIDIZING AGENT

The technology involved in this application is related to that disclosed in the following co-pending U.S. applications filed on even date herewith:

U.S. Ser. No. 08/994,130, U.S. Ser. No. 08/994,446 and U.S. Ser. No. 08/994,444.

The specifications of these related applications are hereby specifically incorporated by reference.

The present invention relates to a ready-to-use composition for the oxidation dyeing of keratin fibers, in particular human keratin fibers such as the hair, this composition comprising, in a medium which is suitable for dyeing, at least one oxidation base in combination with at least one coupler of substituted meta-aminophenol type, at least one cationic direct dye and at least one oxidizing agent. The present invention also relates to the dyeing process using this composition, as well as to a dyeing kit for the preparation of such a ready-to-use composition.

It is known to dye keratin fibers, and in particular human hair, with dye compositions containing oxidation dye precursors, in particular ortho- or para-phenylenediamines, and ortho- or para-aminophenols, which are generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being selected in particular from aromatic meta-diamines, meta-aminophenols, meta-diphenols and certain indole compounds such as 6-hydroxyindole.

The variety of compounds used as regards the oxidation bases and the couplers allows a wide range of colors to be obtained.

It is also known that in order to vary the shades obtained further and to give them glints, it is possible to use, in combination with the oxidation dye precursors and the couplers, direct dyes, i.e., colored substances which provide coloration in the absence of an oxidizing agent.

The so-called "permanent" coloration obtained by means of these oxidation dyes must moreover satisfy a certain number of requirements. Thus, it must be able to give shades of the desired intensity and it must be able to withstand external agents (light, bad weather, washing, permanent waving, perspiration, rubbing).

The great majority of direct dyes belong to the family of nitrobenzene compounds and have the drawback, when they are incorporated into dye compositions, of leading to colorations that have an insufficient endurance, i.e., fastness, in particular with respect to shampoos.

The present invention proposes novel compositions for the oxidation dyeing of keratin fibers, and in particular human keratin fibers such as hair, which make it possible to obtain colorations which are rich in glints while at the same time having good endurance properties in particular.

Thus, the inventors have discovered that it is possible to obtain novel dyes that are both rich in glints and have good endurance by combining:

at least one oxidation base, at least one coupler selected from the substituted meta-aminophenol derivatives of formula (I) below, and the acid-addition salts thereof, at least one cationic direct dye of formula (II) below, and at least one oxidizing agent.

The first subject of the invention is thus a ready-to-use composition for the oxidation dyeing of keratin fibers, and in particular human keratin fibers such as the hair, characterized in that it comprises, in a medium which is suitable for dyeing:

at least one oxidation base, at least one coupler selected from meta-aminophenols of formula (I) below, and the acid-addition salts thereof:

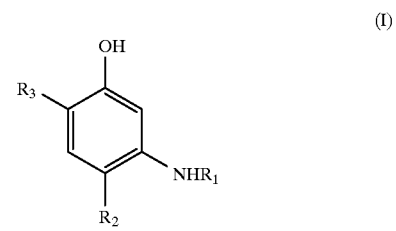

in which:

$R_1$ represents a hydrogen atom or a $C_1$–$C_4$ alkyl, $C_1$–$C_4$ monohydroxyalkyl or $C_2$–$C_4$ polyhydroxylalkyl radical, $R_2$ represents a hydrogen atom, a $C_1$–$C_4$ alkyl or $C_1$–$C_4$ alkoxy radical or a halogen atom selected from chlorine, bromine and fluorine, $R_3$ represents a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkyloxy radical, at least one cationic direct dye selected from the compounds of formula (II) below:

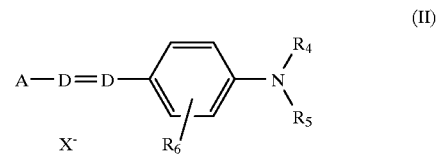

in which:

D independently represents a nitrogen atom or the —CH group, $R_4$ and $R_5$ each independently represents a hydrogen atom; a $C_1$–$C_4$ alkyl radical which may be substituted with a —CN, —OH or —NH$_2$ radical or form, with a carbon atom of the benzene ring, a heterocycle which is optionally oxygenated or nitrogenous, which may be substituted with one or more $C_1$–$C_4$ alkyl radicals; or a 4'-aminophenol radical, $R_6$ represents a hydrogen or halogen atom selected from chlorine, bromine, iodine and fluorine, or a $C_1$–$C_4$ alkoxy or acetyloxy radical, $X^-$ represents an anion preferably selected from chloride, methylsulphate and acetate,
A represents a group selected from the following structures:
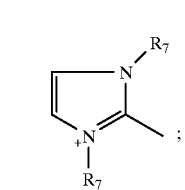
A₁
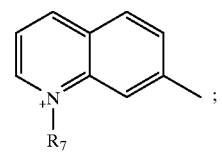
A₂
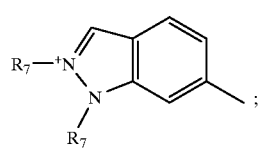
A₃
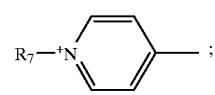
A₄
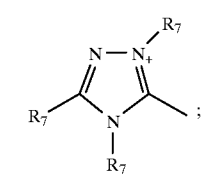
A₅
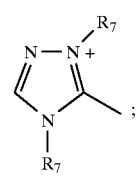
A₆
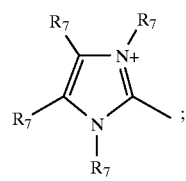
A₇
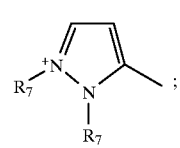
A₈
-continued
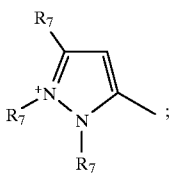
A₉
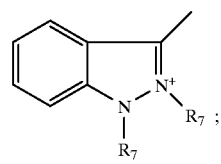
A₁₀
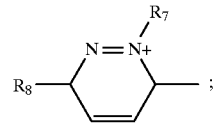
A₁₁
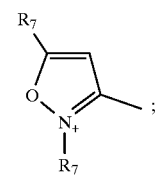
A₁₂
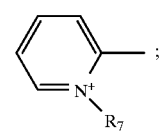
A₁₃
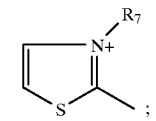
A₁₄
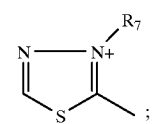
A₁₅
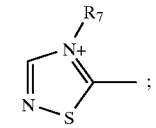
A₁₆
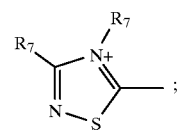
A₁₇

-continued

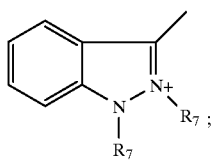
$A_{18}$

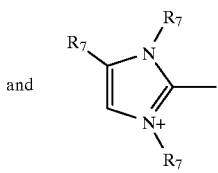
and $A_{19}$ in which:

$R_7$ represents a $C_1$–$C_4$ alkyl radical which may be substituted with a hydroxyl radical, and $R_8$ represents a $C_1$–$C_4$ alkoxy radical, with the proviso that when D represents —CH, A represents $A_4$ or $A_{13}$ and $R_6$ is other than an alkoxy radical, then $R_4$ and $R_5$ do not simultaneously denote a hydrogen atom; and at least one oxidizing agent.

The ready-to-use dye compositions in accordance with the invention make it possible to obtain colorations in red, copper or plum shades which effectively withstand the various treatments to which the hair may be subjected and in particular with regard to shampoos.

A subject of the invention is also a process for the oxidation dyeing of keratin fibers using this ready-to-use dye composition.

The oxidation base(s) which may be used in the ready-to-use dye compositions in accordance with the invention are preferably selected from para-phenylene-diamines, bis(phenyl)alkylenediamines, para-aminophenols, ortho-aminophenols and heterocyclic oxidation bases.

According to a preferred embodiment of the invention, the oxidation base(s) is (are) selected from para-phenylenediamines and para-aminophenols.

Among the para-phenylenediamines which can be used as oxidation bases in the ready-to-use dye compositions in accordance with the invention, mention may be made in particular of the compounds of formula (III) below, and the acid-addition salts thereof:

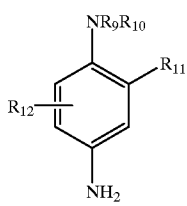
(III)

in which:

$R_9$ represents a hydrogen atom, a $C_1$–$C_4$ alkyl, $C_1$–$C_4$ monohydroxyalkyl, $C_2$–$C_4$ polyhydroxyalkyl, phenyl, 4'-aminophenyl or ($C_1$–$C_4$)alkoxy($C_1$–$C_4$)alkyl radical, $R_{10}$ represents a hydrogen atom or a $C_1$–$C_4$ alkyl, $C_1$–$C_4$ monohydroxyalkyl or $C_2$–$C_4$ polyhydroxyalkyl radical, $R_{11}$ represents a hydrogen atom, a halogen atom such as a chlorine, bromine, iodine or fluorine atom, or a $C_1$–$C_4$ alkyl, $C_1$–$C_4$ monohydroxyalkyl, $C_1$–$C_4$ hydroxyalkoxy, $C_1$–$C_4$ acetylaminoalkoxy, $C_1$–$C_4$ mesylaminoalkoxy or $C_1$–$C_4$ carbamoylaminoalkoxy radical, $R_{12}$ represents a hydrogen atom or a $C_1$–$C_4$ alkyl radical.

Among the para-phenylenediamines of formula (III) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl- 3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine and 2-β-acetylaminoethyloxy-para-phenylenediamine, and the acid-addition salts thereof.

Among the para-phenylenediamines of formula (III) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the acid-addition salts thereof are most particularly preferred.

Among the bis(phenyl)alkylenediamines which can be used as oxidation bases in the ready-to-use dye compositions in accordance with the invention mention may be made in particular of the compounds corresponding to formula (IV) below, and the acid-addition salts thereof:

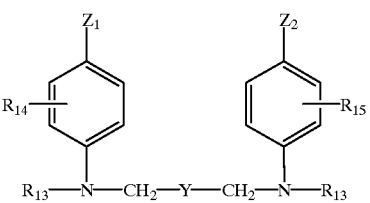
(IV)

in which:

$Z_1$ and $Z_2$ each independently represents a hydroxyl radical or $NHR_{16}$ in which $R_{16}$ represents a hydrogen atom or a $C_1$–$C_4$ alkyl radical, $R_{13}$ independently represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue can be substituted, $R_{14}$ and $R_{15}$ each independently represents a hydrogen or halogen atom or a $C_1$–$C_4$ alkyl radical, Y represents a radical selected from the following radicals:

—$(CH_2)_n$—; —$(CH_2)_m$—O—$(CH_2)_m$—; —$(CH_2)_m$—CHOH—$(CH_2)_m$— and

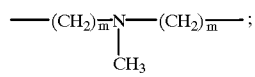

in which:
n is an integer ranging from 0 to 8 and m is an integer ranging from 0 to 4.

Among the bis(phenyl)alkylenediamines of formula (IV) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the acid-addition salts thereof.

Among these bis(phenyl)alkylenediamines of formula (IV), N,N'-bis(β-hydroxyethyl)-N,N'-bis(4'aminophenyl)-1,3-diaminopropanol or one of the acid-addition salts thereof is more particularly preferred.

Among the para-aminophenols which can be used as oxidation bases in the ready-to-use dye compositions in accordance with the invention, mention may be made in particular of the compounds corresponding to formula (V) below, and the acid-addition salts thereof:

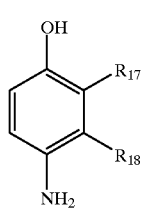

(V)

in which:
$R_{17}$ represents a hydrogen or fluorine atom or a $C_1-C_4$ alkyl, $C_1-C_4$ monohydroxyalkyl, $(C_1-C_4)$alkoxy$(C_1-C_4)$alkyl, $C_1-C_4$ aminoalkyl or hydroxy$(C_1-C_4)$alkylamino-$(C_1-C_4)$alkyl radical,
$R_{18}$ represents a hydrogen or fluorine atom or a $C_1-C_4$-alkyl, $C_1-C_4$ monohydroxyalkyl, $C_2-C_4$ polyhydroxyalkyl, $C_1-C_4$ aminoalkyl, $C_1-C_4$ cyanoalkyl or $(C_1-C_4)$alkoxy-$(C_1-C_4)$alkyl radical,
with the proviso that at least one of the radicals $R_{17}$ or $R_{18}$ represents a hydrogen atom.

Among the para-aminophenols of formula (V) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethyl-phenol, 4-amino-2-aminomethylphenol, 4-amino-2-(β-hydroxyethylaminomethyl)phenol and 4-amino-2-fluoro-phenol, and the acid-addition salts thereof.

Among the ortho-aminophenols which can be used as oxidation bases in the ready-to-use dye compositions in accordance with the invention, mention may be made more particularly of 2-amino-phenol, 2-amino-5-methylphenol, 2-amino-6-methylphenol and 5-acetamido-2-aminophenol, and the acid-addition salts thereof.

Among the heterocyclic bases which can be used as oxidation bases in the ready-to-use dye compositions in accordance with the invention, mention may be made more particularly of pyridine derivatives, pyrimidine derivatives and pyrazole derivatives, and the acid-addition salts thereof.

Among the pyridine derivatives, mention may be made more particularly of the compounds described, for example, in patents GB 1,026,978 and GB 1,153,196, the disclosures of which are specifically incorporated by reference herein, such as 2,5-diaminopyridine, and the acid-addition salts thereof.

Among the pyrimidine derivatives, mention may be made more particularly of the compounds described, for example, in German patent DE 2,359,399 or Japanese patents JP 88-169,571 and JP 91-333,495, the disclosures of which are specifically incorporated by reference herein, such as 2,4,5,6-tetraaminopyrimidine and 4-hydroxy-2,5,6-triaminopyrimidine, and the acid-addition salts thereof.

Among the pyrazole derivatives, mention may be made more particularly of the compounds described in patents DE 3,843,892 and DE 4,133,957 and patent applications WO 94/08969 and WO 94/08970, the disclosures of which are specifically incorporated by reference herein, such as 4,5-diamino-1-methylpyrazole, 3,4-diaminopyrazole and 4,5-diamino-1-(4'-chlorobenzyl) pyrazole, and the acid-addition salts thereof.

Among the meta-aminophenols of formula (I) which can be used as coupler in the ready-to-use dye compositions in accordance with the invention, mention may be made more particularly of 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxy-phenol and 5-(γ-hydroxypropylamino)-2-methylphenol, and the acid-addition salts thereof.

The cationic direct dyes of formula (II) which can be used in the ready-to-use dye compositions in accordance with the invention are known compounds and are described, for example, in patent applications WO 95/01772, WO 95/15144 and EP-A-0,714,954, the disclosures of which are specifically incorporated by reference herein. Among the cationic direct dyes of formula (II) which can be used in the ready-to-use dye compositions in accordance with the invention, mention may be made more particularly of the compounds corresponding to structures (II1) to (II43) below:

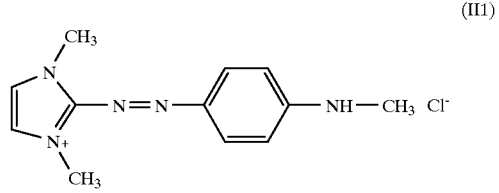

(II1)

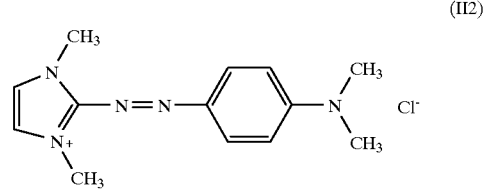

(II2)

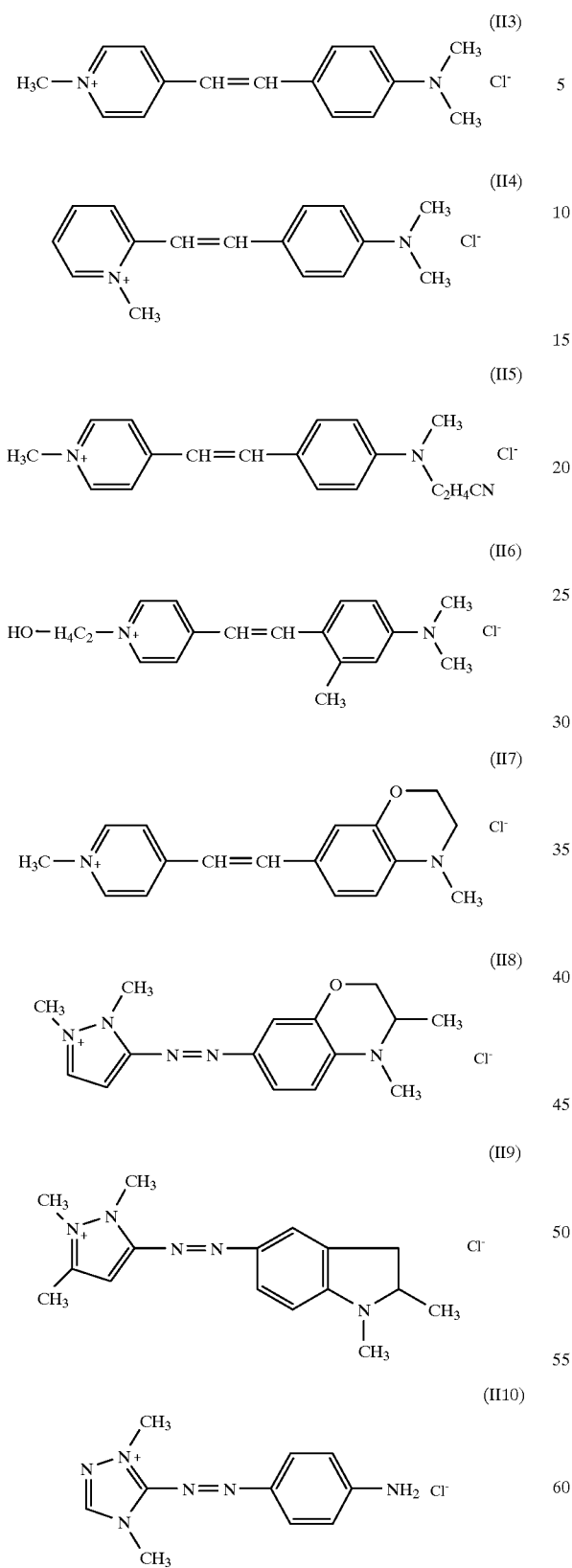
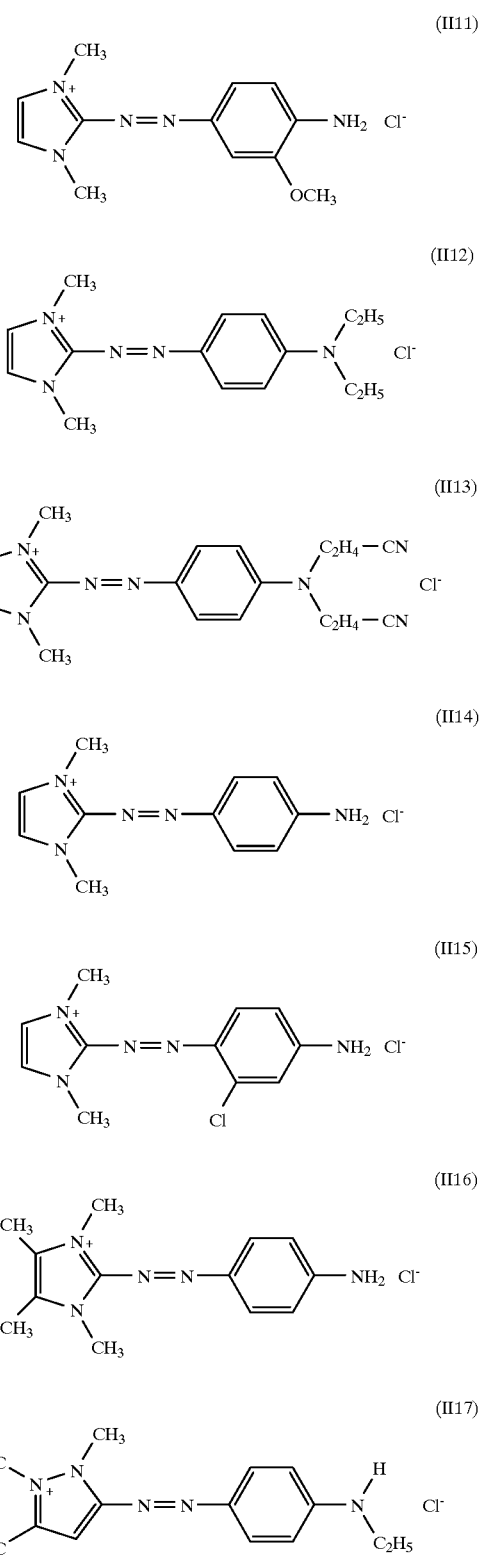

-continued
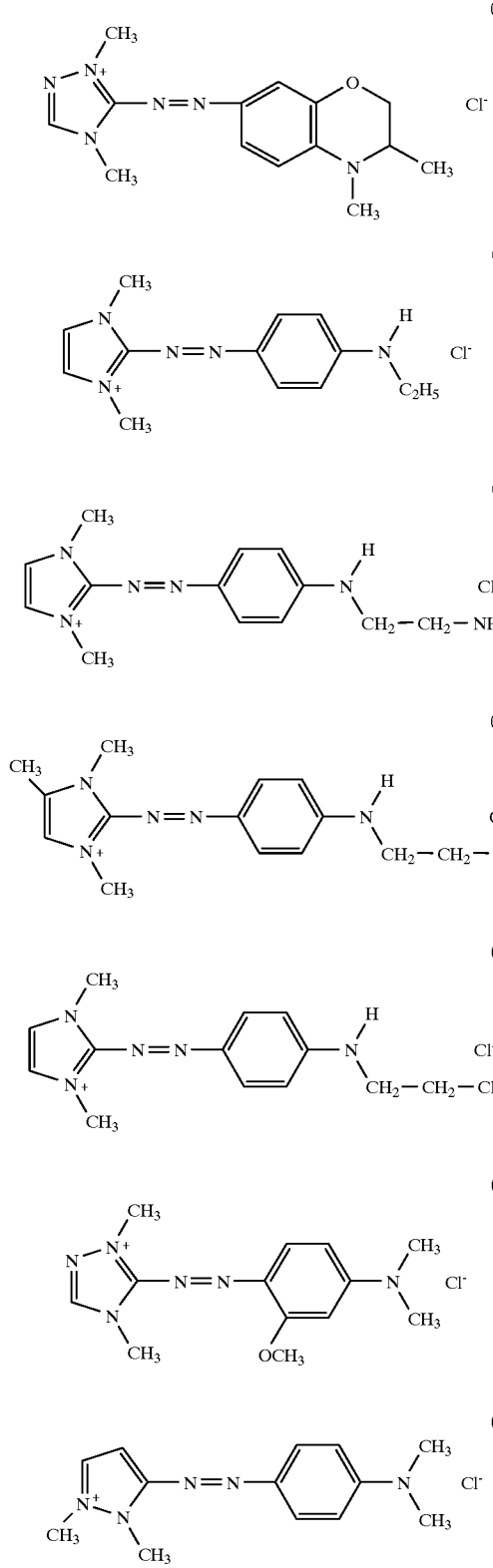
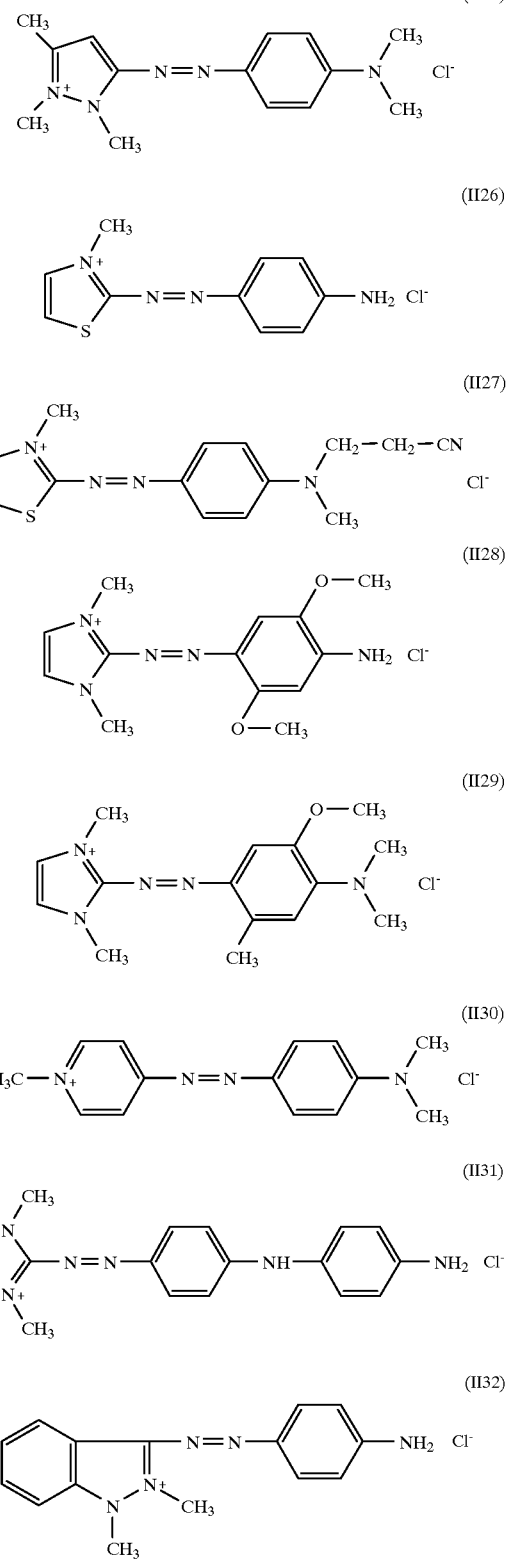

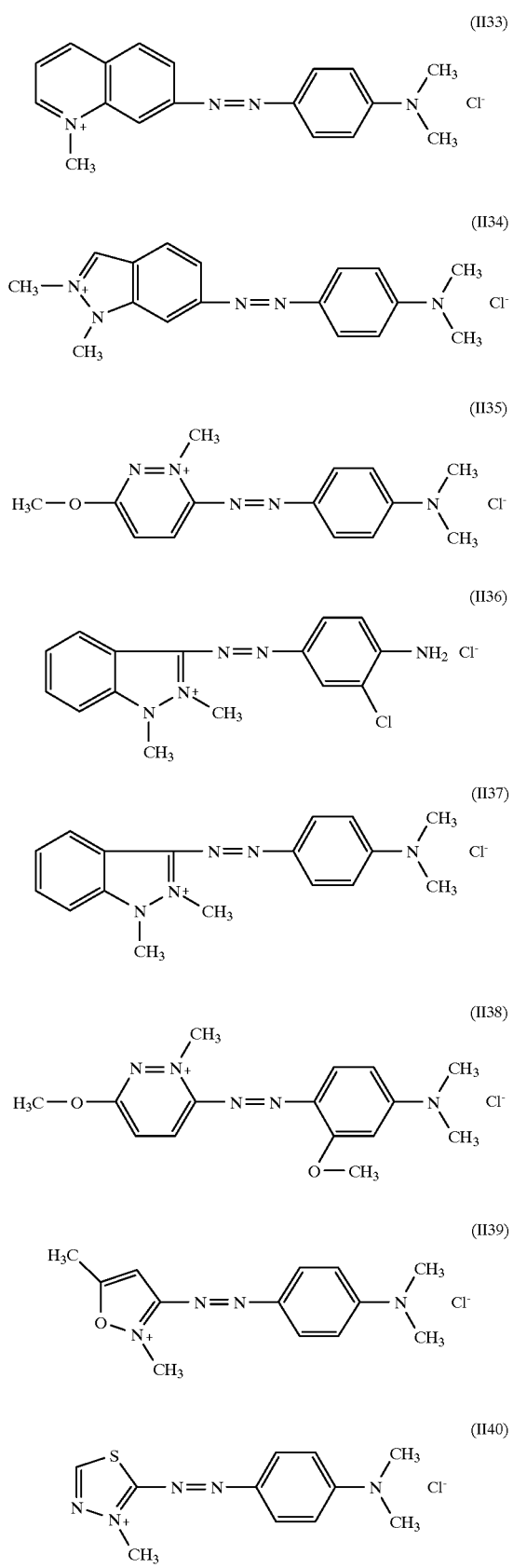
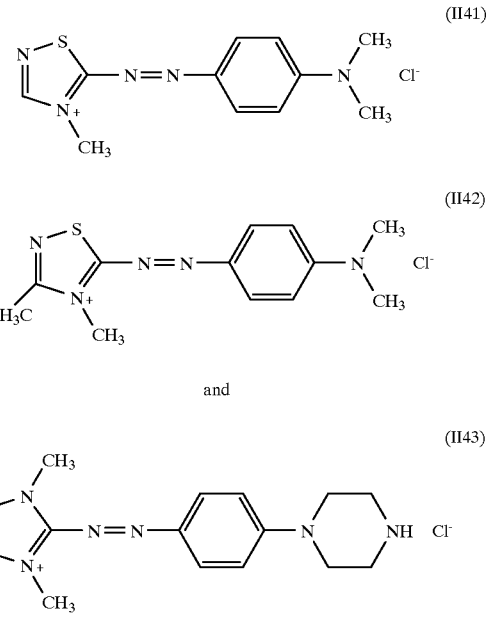

Among the compounds of structures (II1) to (II43) described above, the compounds corresponding to structures (II1), (II2), (II14) and (II31) are more particularly preferred.

The acid-addition salts which can be used in the context of the dye compositions of the invention are selected in particular from the hydrochlorides, hydrobromides, sulphates and tartrates.

The at least one oxidizing agent present in the dye composition is selected from the oxidizing agents used conventionally in oxidation dyeing and preferably from hydrogen peroxide, urea peroxide, alkali metal bromates and persalts such as perborates and persulphates. Hydrogen peroxide is particularly preferred.

The oxidation base(s) preferably represents from approximately 0.0001 to approximately 10% by weight relative to the total weight of the ready-to-use dye composition, and even more preferably from approximately 0.001 to approximately 5% by weight, relative to the total weight of the ready-to-use dye composition.

The meta-aminophenol(s) of formula (I) as defined above preferably represents from approximately 0.0001 to approximately 5% by weight relative to the total weight of the ready-to-use dye composition, and even more preferably from approximately 0.005 to approximately 3% by weight relative to the total weight of the ready-to-use dye composition.

The cationic direct dye(s) of formula (II) in accordance with the invention preferably represents from approximately 0.001 to approximately 10% by weight relative to the total weight of the ready-to-use dye composition, and even more preferably from approximately 0.05 to approximately 2% by weight relative to the total weight of the ready-to-use dye composition.

The pH of the dye composition as defined above generally ranges from approximately 5 to approximately 12. It can be adjusted to the desired value using acidifying or basifying agents usually used in the dyeing of keratin fibers.

Among the acidifying agents, mention may be made, by way of example, of inorganic or organic acids such as hydrochloric acid, orthophosphoric acid, carboxylic acids such as tartaric acid, citric acid or lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (VI) below:

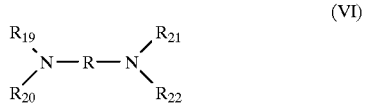

in which:

R is a propylene residue optionally substituted with a hydroxyl group or a $C_1$–$C_4$ alkyl radical; and $R_{19}$, $R_{20}$, $R_{21}$ and $R_{22}$ each independently represent a hydrogen atom or a $C_1$–$C_4$ alkyl or $C_1$–$C_4$ hydroxyalkyl radical.

In addition to the dyes defined above, the dye composition in accordance with the invention may also contain other couplers and/or direct dyes.

The medium which is suitable for dyeing (or the support) for the ready-to-use dye composition in accordance with the invention generally comprises water or a mixture of water and at least one organic solvent in order to dissolve the compounds which would not be sufficiently soluble in water. By way of organic solvent, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably ranging from approximately 1 to approximately 40% by weight relative to the total weight of the dye composition, and even more preferably from approximately 5 to approximately 30% by weight relative to the total weight of the dye composition.

The ready-to-use dye compositions in accordance with the invention may also contain various adjuvants used conventionally in compositions for dyeing the hair, such as anionic, cationic, nonionic or amphoteric surfactants or mixtures thereof, anionic, cationic, nonionic or amphoteric polymers or mixtures thereof, inorganic or organic thickeners, antioxidants, penetration agents, sequestering agents, fragrances, buffers, dispersing agents, packaging agents, film-forming agents, preserving agents and opacifiers.

Needless to say, a person skilled in the art will take care to select the optional additional compound(s) mentioned above such that the advantageous properties intrinsically associated with the ready-to-use dye composition in accordance with the invention are not, or are not substantially, adversely affected by the addition(s) envisaged.

The ready-to-use dye compositions in accordance with the invention can be in various forms, such as in the form of liquids, creams or gels or in any other form which is appropriate for dyeing keratin fibers, and in particular human hair.

A subject of the invention is also a process for dyeing keratin fibers, and in particular human keratin fibers such as the hair, using the ready-to-use dye composition as defined above.

According to this process, the ready-to-use dye composition as defined above is applied to the fibers and is left on them for an exposure time preferably of from approximately 3 to approximately 40 minutes, more preferably of from approximately 5 to approximately 30 minutes, after which the fibers are rinsed, optionally washed with shampoo, rinsed again and dried.

According to a first preferred embodiment, the process includes a preliminary step which includes separately storing, on the one hand, a composition (A) comprising, in a medium which is suitable for dyeing, at least one oxidation base, at least one coupler selected from the meta-aminophenols of formula (I) as defined above and at least one cationic direct dye selected from the compounds of formula (II) as defined above, and, on the other hand, a composition (B) containing, in a medium which is suitable for dyeing, at least one oxidizing agent as defined above, and in mixing them together at the time of use before applying this mixture to the keratin fibers.

According to a second preferred embodiment, the process includes a preliminary step which includes separately storing, on the one hand, a composition (A) comprising, in a medium which is suitable for dyeing, at least one oxidation base, at least one coupler selected from the meta-aminophenols of formula (I) as defined above; on the other hand, a composition (A') comprising, in a medium which is suitable for dyeing, at least one cationic direct dye selected from the compounds of formula (II) as defined above, and, lastly, a composition (B) containing, in a medium which is suitable for dyeing, at least one oxidizing agent as defined above, and in mixing them together at the time of use before applying this mixture to the keratin fibers.

The composition (A') used according to this second variant of the process in accordance with the invention can optionally be in powder form, the cationic direct dye(s) of formula (II) in accordance with the invention itself (themselves) constituting, in this case, all of the compositions (A') or optionally being dispersed in an organic and/or inorganic pulverulent excipient.

When it is present in the composition A', the organic excipient can be of synthetic or plant origin and is selected in particular from crosslinked and non-crosslinked synthetic polymers, polysaccharides such as celluloses and modified or unmodified starches, as well as natural products containing them such as sawdust and plant gums (guar gum, carob gum, xanthan gum, etc.).

When it is present in the composition (A'), the inorganic excipient can contain metal oxides such as titanium oxides, aluminium oxides, kaolin, talc, silicates, mica and silicas.

An advantageous excipient preferred according to the invention is sawdust.

The powdered composition (A') may also contain binders or coating products in an amount which preferably does not exceed approximately 3% by weight relative to the total weight of the said composition (A').

These binders are preferably selected from oils and liquid fatty substances of inorganic, synthetic, animal or plant origin.

The composition (A') may optionally also contain other adjuvants, in powdered form, in particular surfactants of any nature, hair conditioners such as, for example, cationic polymers, etc.

Another subject of the invention is a multi-compartment dyeing "kit" or device or any other multi-compartment packaging system, a first compartment of which contains the composition (A) as defined above, an optional second compartment contains the composition (A') as defined above, when it is present, and a third compartment contains the oxidizing composition (B) as defined above. These devices can be equipped with means which allow the desired mixture to be applied to the hair, such as the devices described in patent FR-A-2,586,913, the disclosure of which is specifically incorporated by reference herein.

The examples which follow are intended to illustrate the invention without, however, limiting its scope.

EXAMPLES 1 TO 4

Compositions 1 (A) to 4 (A) below, in accordance with the invention, were prepared (contents in grams):

| COMPOSITION | 1 (A) | 2 (A) | 3 (A) | 4 (A) |
|---|---|---|---|---|
| Para-toluylenediamine | 0.25 | — | — | — |
| Para-aminophenol | 0.30 | 0.50 | 0.15 | — |
| Para-phenylenediamine | — | 0.20 | — | 0.30 |
| 5-N-(β-Hydroxyethyl)amino-2-methylphenol | 0.5 | 0.8 | 0.17 | — |
| 5-Amino-2-methylphenol | — | — | — | 0.30 |
| Cationic dye of structure (II2) | 0.15 | — | — | — |
| Cationic dye of structure (II14) | — | 0.20 | 0.05 | — |
| Cationic dye of structure (II1) | — | — | — | 0.1 |
| Common dye support (*) | (*) | (*) | (*) | (*) |
| Water qs | 100 g | 100 g | 100 g | 100 g |

| (*)Common dye support: | | |
|---|---|---|
| Oleyl alcohol polyglycerolated with 2 mol of glycerol | 4.0 | g |
| Oleyl alcohol polyglycerolated with 4 mol of glycerol, containing 78% active material (A.M.) | 5.69 | g A.M. |
| Oleic acid | 3.0 | g |
| Oleylamine containing 2 mol of ethylene oxide, sold under the trade name Ethomeen O12 by the company Akzo | 7.0 | g |
| Diethylaminopropyl laurylaminosuccinamate, sodium salt, containing 55% A.M. | 3.0 | g A.M. |
| Oleyl alcohol | 5.0 | g |
| Oleic acid diethanolamide | 12.0 | g |
| Propylene glycol | 3.5 | g |
| Ethyl alcohol | 7.0 | g |
| Dipropylene glycol | 0.5 | g |
| Propylene glycol monomethyl ether | 9.0 | g |
| Sodium metabisulphite as an aqueous solution containing 35% A.M. | 0.455 | g A.M. |
| Ammonium acetate | 0.8 | g |
| Antioxidant, sequestering agent | qs | |
| Fragrance, preserving agent | qs | |
| Aqueous ammonia containing 20% NH$_3$ | 10.0 | g |

Each of these compositions 1 (A) to 4 (A) was mixed, at the time of use, with an equal amount of a composition (B) comprising a 20-volumes hydrogen peroxide solution (6% by weight).

Each resulting composition (ready-to-use composition in accordance with the invention) was applied for 30 minutes to locks of natural grey hair containing 90% white hairs. The locks of hair were then rinsed, washed with a standard shampoo and then dried.

The locks of hair were dyed in the shades given in the table below:

| EXAMPLE [COMPOSITION] | SHADE OBTAINED |
|---|---|
| 1 [1 (A)] | Dark blond with intense red glint |
| 2 [2 (A)] | Blond with intense coppery-red glint |
| 3 [3 (A)] | Light blond with copper-red glint |
| 4 [4 (A)] | Blond with red-plum glint |

The shades obtained had very good endurance to subsequent shampooing.

According to a variant of the invention, the cationic direct dyes of structures (II2), (II14) and (II1) can be incorporated into the dye compositions 1 (A), 2 (A), 3 (A) and 4 (A) at the time of use.

EXAMPLE 5

| Composition 5 (A) was prepared: | |
|---|---|
| 1,4-Diaminobenzene | 0.40 g |
| 5-Amino-2-methylphenol | 0.45 g |
| Common dye support as described above for Examples 1 to 4 | (*) |
| Demineralized water qs | 100 g |
| Composition 5 (A') was prepared: | |
| Cationic dye of structure (II2) | 4 g |
| Quaternary polyammonium sold under trade name CELQUAT SC-240 by the company National Starch | 10 g |
| Sawdust qs | 100 g |

One part by weight of composition 5 (A) above was mixed, at the time of use, with 0.1 part by weight of composition 5 (A') and with one part by weight of a composition (B) comprising a 20-volumes hydrogen peroxide solution (6% by weight).

The resulting composition was applied for 30 minutes to locks of natural grey hair containing 90% white hairs. The hair was then rinsed, washed with a standard shampoo and then dried.

The hair was dyed in a light chestnut shade with intense red glints which had very good endurance properties with respect to subsequent shampooing.

We claim:

1. A ready-to-use composition for the oxidation dyeing of keratin fibers, comprising, in a medium suitable for dyeing:

at least one oxidation base, at least one coupler selected from meta-aminophenols of formula (I), or the acid-addition salts thereof:

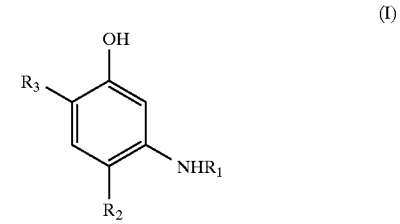

(I)

in which:

R$_1$ represents a hydrogen atom or a C$_1$–C$_4$ alkyl, C$_1$–C$_4$ monohydroxyalkyl or C$_2$–C$_4$ polyhydroxyalkyl radical, R$_2$ represents a hydrogen atom, a C$_1$–C$_4$ alkyl or C$_1$–C$_4$ alkoxy radical or a halogen atom, R$_3$ represents a C$_1$–C$_4$ alkyl, C$_1$–C$_4$ alkoxy, C$_1$–C$_4$ monohydroxyalkyl, C$_2$–C$_4$ polyhydroxyalkyl, C$_1$–C$_4$ mono-hydroxyalkoxy or C$_2$–C$_4$ polyhydroxyalkoxy radical, at least one cationic direct dye selected from compounds of formula (II):

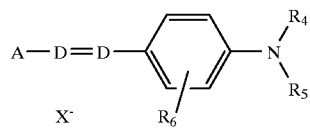

(II)

in which:
- D independently represents a nitrogen atom or a —CH group,
- $R_4$ and $R_5$ each independently represents a hydrogen atom; a $C_1$–$C_4$ alkyl radical which may be substituted with a —CN, —OH or —NH$_2$ radical or form, with a carbon atom of the benzene ring, a heterocycle which is optionally oxygenated or nitrogenous, which may be substituted with one or more $C_1$–$C_4$ alkyl radicals; or a 4'-aminophenyl radical,
- $R_6$ represents a hydrogen or halogen atom, or a $C_1$–$C_4$ alkoxy or acetyloxy radical,
- $X^-$ represents an anion selected from chloride, methylsulphate or acetate, and
- A represents a group selected from the following structures:

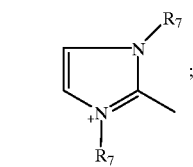 $A_1$

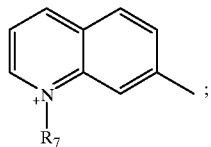 $A_2$

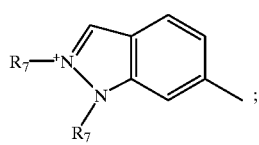 $A_3$

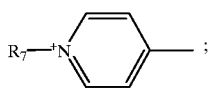 $A_4$

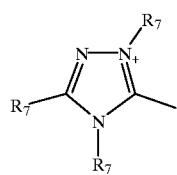 $A_5$

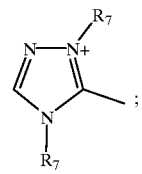 $A_6$

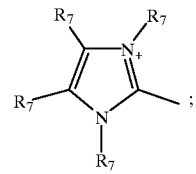 $A_7$

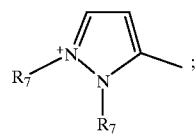 $A_8$

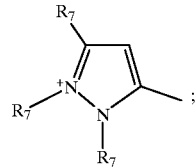 $A_9$

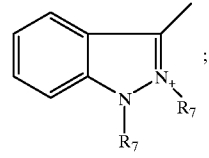 $A_{10}$

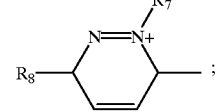 $A_{11}$

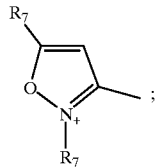 $A_{12}$

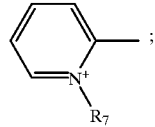 $A_{13}$

-continued

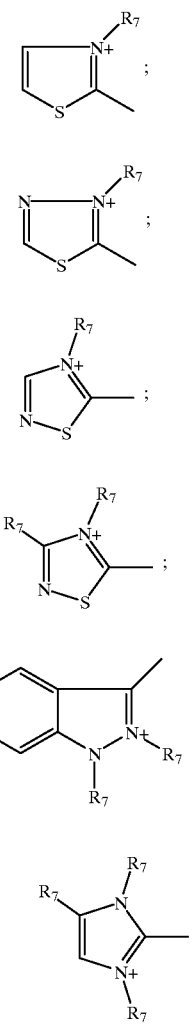

in which:
R$_7$ represents a C$_1$–C$_4$ alkyl radical which may be substituted with a hydroxyl radical, and
R$_8$ represents a C$_1$–C$_4$ alkoxy radical,
with the proviso that when D represents —CH, A represents A$_4$ or A$_{13}$ and R$_6$ is other than an alkoxy radical, then R$_4$ and R$_5$ do not simultaneously denote a hydrogen atom; and
at least one oxidizing agent.

2. A ready-to-use composition for the oxidation dyeing of keratin fibers according to claim 1, wherein said keratin fibers are human hair.

3. A ready-to-use composition for the oxidation dyeing of keratin fibers according to claim 1, wherein, with respect to R$_2$, said halogen is selected from chlorine, bromine or fluorine.

4. A ready-to-use composition for the oxidation dyeing of keratin fibers according to claim 1, wherein, with respect to R$_6$, said halogen is selected from chlorine, bromine, iodine or fluorine.

5. A ready-to-use composition for the oxidation dyeing of keratin fibers according to claim 1, wherein said at least one oxidation base is selected from para-phenylenediamines, bis(phenyl)alkylenediamines, para-aminophenols, ortho-aminophenols or heterocyclic oxidation bases.

6. A ready-to-use composition for the oxidation dyeing of keratin fibers according to claim 5, wherein said at least one oxidation base is selected from para-phenylenediamines or para-aminophenols.

7. A ready-to-use composition for the oxidation dyeing of keratin fibers according to claim 6, wherein said para-phenylenediamines are selected from the compounds of formula (III), or the acid-addition salts thereof:

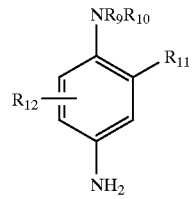

(III)

in which:
R$_9$ represents a hydrogen atom, a C$_1$–C$_4$ alkyl, C$_1$–C$_4$ monohydroxyalkyl, C$_2$–C$_4$ polyhydroxyalkyl, phenyl, 4'-aminophenyl or (C$_1$–C$_4$)alkoxy(C$_1$–C$_4$)alkyl radical,
R$_{10}$ represents a hydrogen atom or a C$_1$–C$_4$ alkyl, C$_1$–C$_4$ monohydroxyalkyl or C$_2$–C$_4$ polyhydroxyalkyl radical,
R$_{11}$ represents a hydrogen atom, a halogen atom, or a C$_1$–C$_4$ alkyl, C$_1$–C$_4$ monohydroxyalkyl, C$_1$–C$_4$ hydroxyalkoxy, C$_1$–C$_4$ acetylaminoalkoxy, C$_1$–C$_4$ mesylaminoalkoxy or C$_1$–C$_4$ carbamoylaminoalkoxy radical, and
R$_{12}$ represents a hydrogen atom or a C$_1$–C$_4$ alkyl radical.

8. A ready-to-use composition for the oxidation dyeing of keratin fibers according to claim 7, wherein, with respect to R$_{11}$, said halogen atom is selected from chlorine, bromine, iodine or fluorine.

9. A ready-to-use composition for the oxidation dyeing of keratin fibers according to claim 7, wherein said para-phenylenediamines of formula (III) are selected from:
para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
2,5-dimethyl-para-phenylenediamine,
N,N-dimethyl-para-phenylenediamine,
N,N-diethyl-para-phenylenediamine,
N,N-dipropyl-para-phenylenediamine,
4-amino-N,N-diethyl-3-methylaniline,
N,N-bis(β-hydroxyethyl)-para-phenylenediamine,
4-amino-N,N-bis(β-hydroxyethyl)-3-methylaniline,
4-amino-3-chloro-N,N-bis(β-hydroxyethyl)aniline,
2-β-hydroxyethyl-para-phenylenediamine,
2-fluoro-para-phenylenediamine,
2-isopropyl-para-phenylenediamine,
N-(β-hydroxypropyl)-para-phenylenediamine,
2-hydroxymethyl-para-phenylenediamine,
N,N-dimethyl-3-methyl-para-phenylenediamine,
N,N-(ethyl-β-hydroxyethyl)-para-phenylenediamine,
N-(β,γ-dihydroxypropyl)-para-phenylenediamine,
N-(4'-aminophenyl)-para-phenylenediamine,
N-phenyl-para-phenylenediamine, 2-β-hydroxyethyloxy-para-phenylenediamine,
2-β-acetylaminoethyloxy-para-phenylenediamine,
or the acid-addition salts thereof.

10. A ready-to-use composition for the oxidation dyeing of keratin fibers according to claim 9, wherein said para-phenylenediamines of formula (III) are selected from:
para-phenylenediamine,
para-toluylenediamine,
2-chloro-para-phenylenediamine,
2,3-dimethyl-para-phenylenediamine,
2,6-dimethyl-para-phenylenediamine,
2,6-diethyl-para-phenylenediamine,
N,N-bis(β-hydroxyethyl)-para-phenylenediamine,
2-β-hydroxyethyl-para-phenylenediamine,
2-isopropyl-para-phenylenediamine,
2-β-hydroxyethyloxy-para-phenylenediamine,
or the acid-addition salts thereof.

11. A ready-to-use composition for the oxidation dyeing of keratin fibers according to claim 5, wherein said bis(phenyl)alkylenediamines are selected from the compounds of formula (IV), or the acid-addition salts thereof:

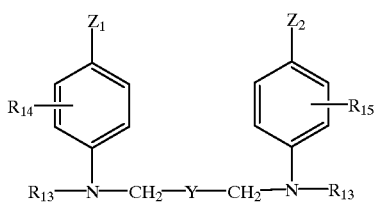

(IV)

in which:
Z$_1$ and Z$_2$ each independently represents a hydroxyl radical or NHR$_{16}$ in which R$_{16}$ represents a hydrogen atom or a C$_1$–C$_4$ alkyl radical,
R$_{13}$ independently represents a hydrogen atom or a C$_1$–C$_4$ alkyl, C$_1$–C$_4$ monohydroxyalkyl or C$_2$–C$_4$ polyhydroxyalkyl radical or a C$_1$–C$_4$ aminoalkyl radical in which the amino portion of said aminoalkyl radical can be substituted,
R$_{14}$ and R$_{15}$ each independently represents a hydrogen or halogen atom or a C$_1$–C$_4$ alkyl radical,
Y represents a radical selected from:

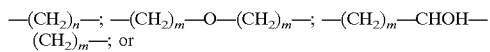

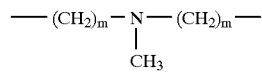

in which:
n is an integer ranging from 0 to 8 and m is an integer ranging from 0 to 4.

12. A ready-to-use composition for the oxidation dyeing of keratin fibers according to claim 11, wherein said bis(phenyl)alkylenediamines of formula (IV) are selected from:

N,N'-bis(β-hydroxyethyl)-N,N'-bis(4'-aminophenyl)-1,3-diaminopropanol,
N,N'-bis(β-hydroxyethyl)-N,N'-bis(4'-aminophenyl) ethylenediamine,
N,N'-bis(4-aminophenyl)tetramethylenediamine,
N,N'-bis(β-hydroxyethyl)-N,N'-bis(4-aminophenyl) tetramethylenediamine, N,N'-bis(4-methylaminophenyl)tetramethylenediamine and
N,N'-bis(ethyl)-N,N'-bis(4'-amino-3'-methylphenyl) ethylenediamine,
or the acid-addition salts thereof.

13. A ready-to-use composition for the oxidation dyeing of keratin fibers according to claim 12, wherein said bis(phenyl)alkylenediamines of formula (IV) are selected from:
N,N'-bis(β-hydroxyethyl)-N,N'-bis(4'-aminophenyl)-1,3-diaminopropanol or the acid-addition salts thereof.

14. A ready-to-use composition for the oxidation dyeing of keratin fibers according to claim 5, wherein said para-aminophenols are selected from compounds of formula (V), or the acid-addition salts thereof:

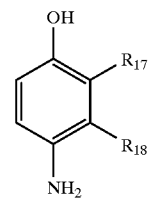

(V)

in which:
R$_{17}$ represents a hydrogen or fluorine atom or a C$_1$–C$_4$ alkyl, C$_1$–C$_4$ monohydroxyalkyl, (C$_1$–C$_4$)alkoxy (C$_1$–C$_4$)alkyl, C$_1$–C$_4$ aminoalkyl or hydroxy(C$_1$–C$_4$) alkylamino-(C$_1$–C$_4$)alkyl radical,
R$_{18}$ represents a hydrogen or fluorine atom or a C$_1$–C$_4$-alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy-(C$_1$–C$_4$)alkyl radical,
and wherein at least one of the radicals R$_{17}$ and R$_{18}$ represents a hydrogen atom.

15. A ready-to-use composition for the oxidation dyeing of keratin fibers according to claim 14, wherein said para-aminophenols of formula (V) are selected from:
para-aminophenol,
4-amino-3-methylphenol,
4-amino-3-fluorophenol,
4-amino-3-hydroxymethylphenol,
4-amino-2-methylphenol,
4-amino-2-hydroxymethylphenol,
4-amino-2-methoxymethylphenol,
4-amino-2-aminomethylphenol,
4-amino-2-(β-hydroxyethylaminomethyl)phenol,
4-amino-2-fluorophenol,
or the acid-addition salts thereof.

16. A ready-to-use composition for the oxidation dyeing of keratin fibers according to claim 5, wherein said ortho-aminophenols are selected from 2-aminophenol, 2-amino-5-methylphenol, 2-amino-6-methylphenol, 5-acetamido-2-aminophenol, or the acid-addition salts thereof.

17. A ready-to-use composition for the oxidation dyeing of keratin fibers according to claim 5, wherein said heterocyclic bases are selected from pyridine derivatives, pyrimidine derivatives, pyrazole derivatives, or the acid-addition salts thereof.

18. A ready-to-use composition for the oxidation dyeing of keratin fibers according to claim 1, wherein said meta-aminophenols of formula (I) are selected from:

5-amino-2-methoxyphenol,
5-amino-2-(β-hydroxyethyloxy)phenol,
5-amino-2-methylphenol,
5-N-(β-hydroxyethyl)amino-2-methylphenol,
5-N-(β-hydroxyethyl)amino-4-methoxy-2-methylphenol,
5-amino-4-methoxy-2-methylphenol,
5-amino-4-chloro-2-methylphenol,
5-amino-2,4-dimethoxy-phenol,
5-(γ-hydroxypropylamino)-2-methylphenol, or the acid-addition salts thereof.

19. A ready-to-use composition for the oxidation dyeing of keratin fibers according to claim 1, wherein said at least one cationic direct dye selected from compounds of formula (II) is selected from the compounds corresponding to structures (II1) to (II43):

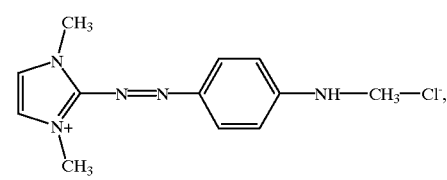
(II1)

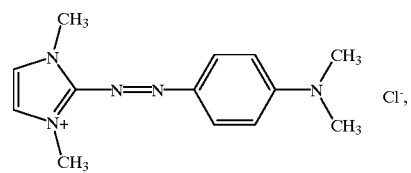
(II2)

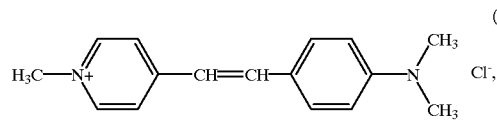
(II3)

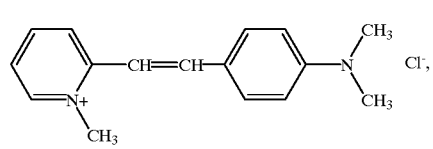
(II4)

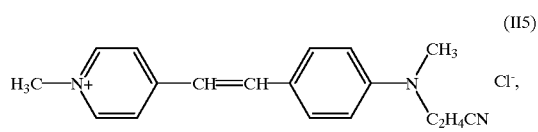
(II5)

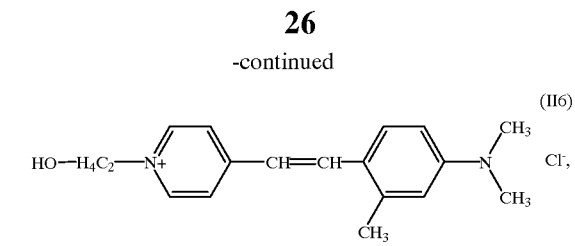
(II6)

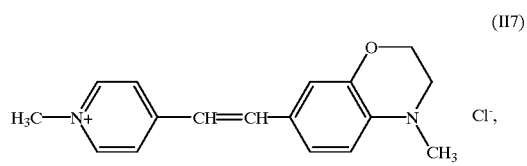
(II7)

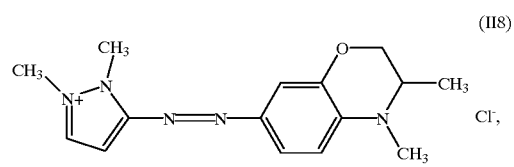
(II8)

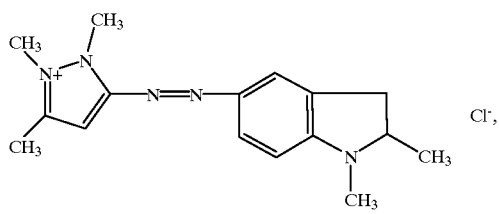
(II9)

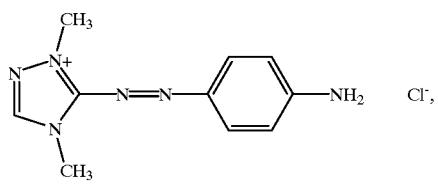
(II10)

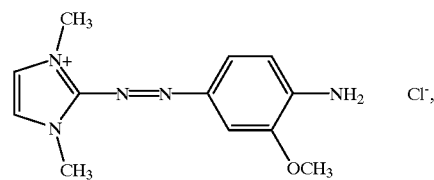
(II11)

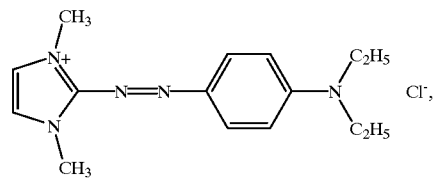
(II12)

(II13)
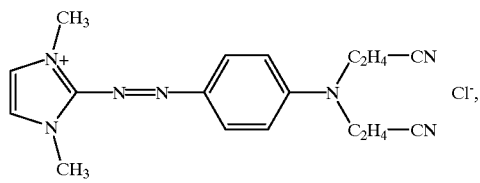
(II14)
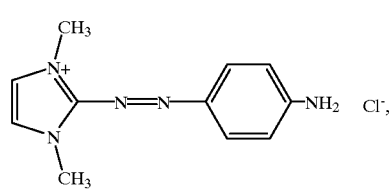
(II15)
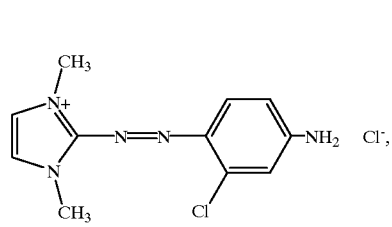
(II16)
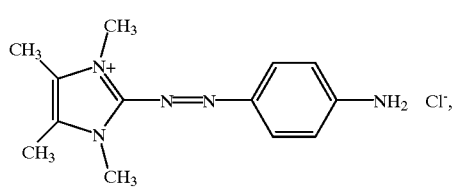
(II17)
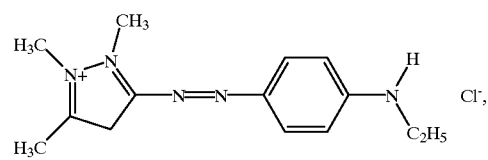
(II18)
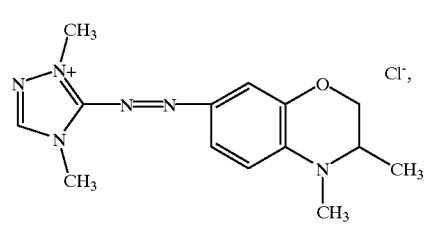
(II19)
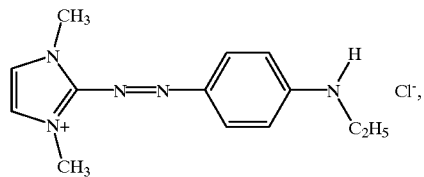
(II20)
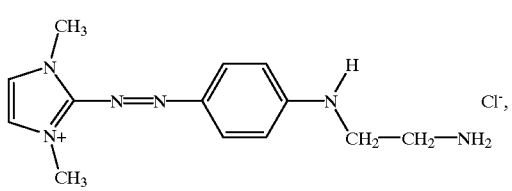
(II21)
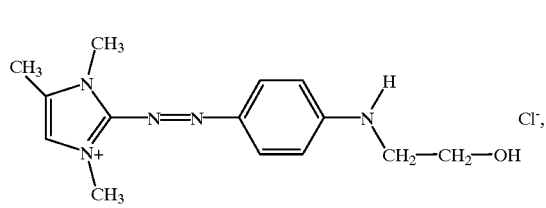
(II22)
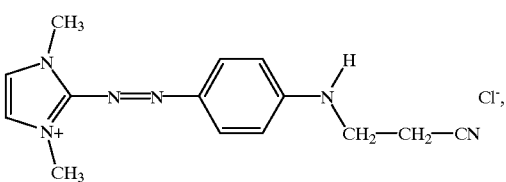
(II23)
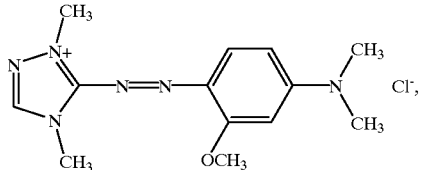
(II24)
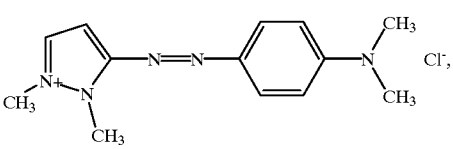

-continued
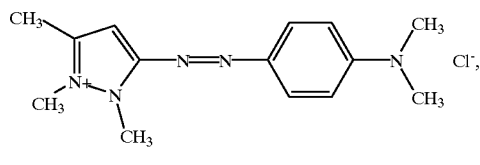 (II25)
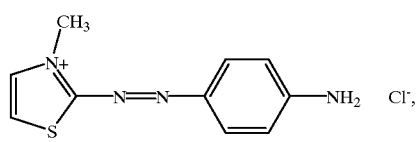 (II26)
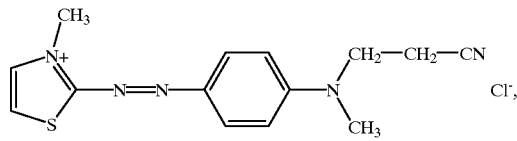 (II27)
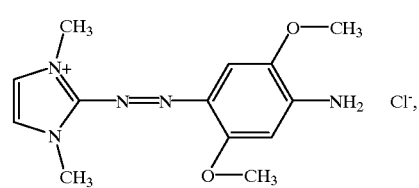 (II28)
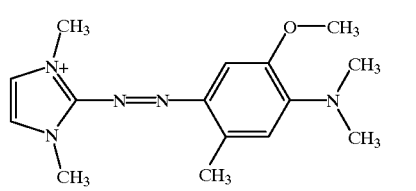 (II29)
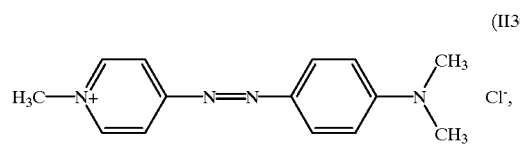 (II30)
-continued
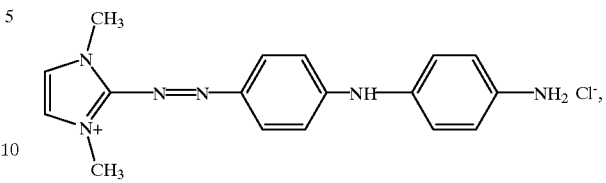 (II31)
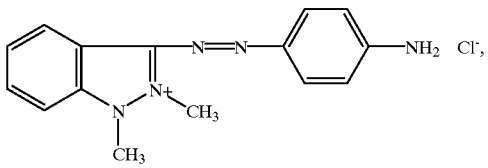 (II32)
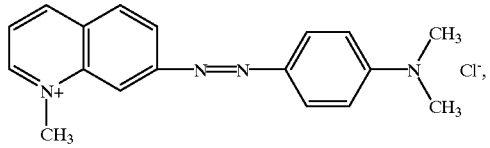 (II33)
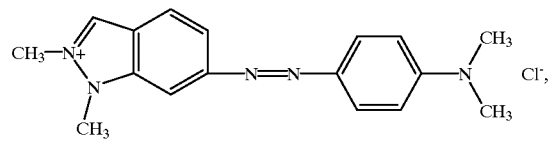 (II34)
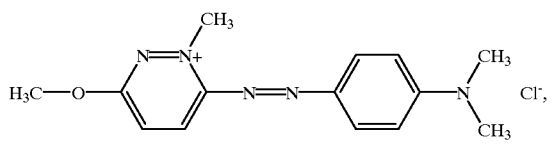 (II35)
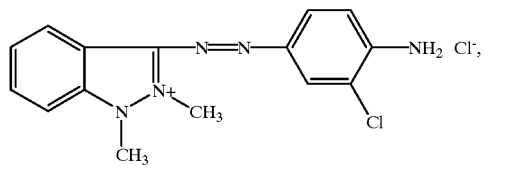 (II36)

(II37)
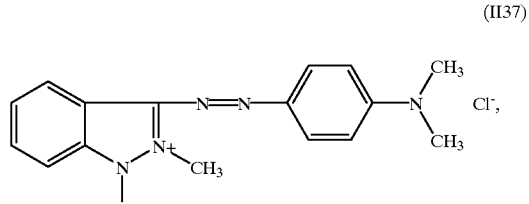

(II38)
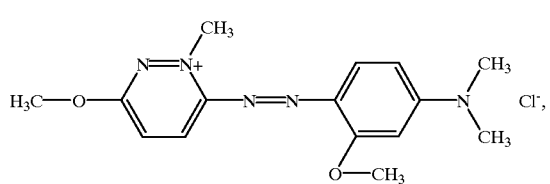

(II39)
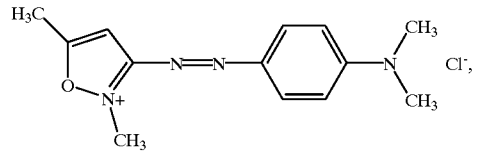

(II40)
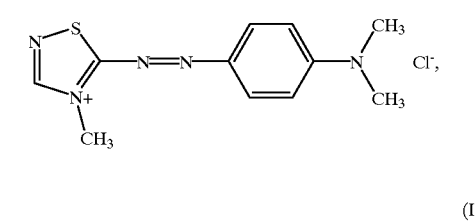

(II41)
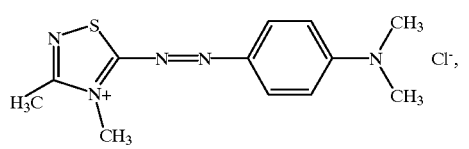

(II42)

or (II43)
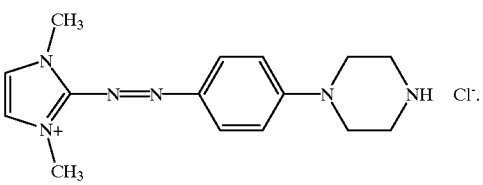

20. A ready-to-use composition for the oxidation dyeing of keratin fibers according to claim 19, wherein said at least one cationic direct dye selected from compounds of formula (II) is selected from the compounds corresponding to structures (II1), (II2), (II14) or (II31).

21. A ready-to-use composition for the oxidation dyeing of keratin fibers according to claim 1, wherein said acid-addition salts are selected from hydrochlorides, hydrobromides, sulphates or tartrates.

22. A ready-to-use composition for the oxidation dyeing of keratin fibers according to claim 1, wherein said at least one oxidizing agent is selected from hydrogen peroxide, urea peroxide, alkali metal bromates or persalts.

23. A ready-to-use composition for the oxidation dyeing of keratin fibers according to claim 22, wherein said persalts are selected from perborates or persulphates.

24. A ready-to-use composition for the oxidation dyeing of keratin fibers according to claim 22, wherein said at least one oxidizing agent is hydrogen peroxide.

25. A ready-to-use composition for the oxidation dyeing of keratin fibers according to claim 1, wherein said at least one oxidation base is present in a concentration ranging from 0.0001 to 10% by weight relative to the total weight of the ready-to-use dye composition.

26. A ready-to-use composition for the oxidation dyeing of keratin fibers according to claim 25, wherein said at least one oxidation base is present in a concentration ranging from 0.001 to 5% by weight relative to the total weight of the ready-to-use dye composition.

27. A ready-to-use composition for the oxidation dyeing of keratin fibers according to claim 1, wherein said at least one coupler is present in a concentration ranging from 0.0001 to 5% by weight relative to the total weight of the ready-to-use dye composition.

28. A ready-to-use composition for the oxidation dyeing of keratin fibers according to claim 27, wherein said at least one coupler is present in a concentration ranging from 0.005 to 3% by weight relative to the total weight of the ready-to-use dye composition.

29. A ready-to-use composition for the oxidation dyeing of keratin fibers according to claim 1, wherein said at least one cationic direct dye is present in a concentration ranging from 0.001 to 10% by weight relative to the total weight of the ready-to-use dye composition.

30. A ready-to-use composition for the oxidation dyeing of keratin fibers according to claim 29, wherein said at least one cationic direct dye is present in a concentration ranging from 0.05 to 2% by weight relative to the total weight of the ready-to-use dye composition.

31. A ready-to-use composition for the oxidation dyeing of keratin fibers according to claim 1, wherein said ready-to-use composition has a pH ranging from 5 to 12.

32. A ready-to-use composition for the oxidation dyeing of keratin fibers according to claim 1, wherein said medium suitable for dyeing comprises water or a mixture of water and at least one organic solvent.

33. A ready-to-use composition for the oxidation dyeing of keratin fibers according to claim 32, wherein said at least one organic solvent is present in a concentration ranging from 1 to 40% by weight, relative to the total weight of the ready-to-use dye composition.

34. A ready-to-use composition for the oxidation dyeing of keratin fibers according to claim 1, wherein said ready-to-use composition is in the form of a liquid, a cream, a gel, or any form suitable for dyeing keratin fibers.

35. A process for dyeing keratin fibers comprising applying at least one ready-to-use dye composition according to claim 1 to said keratin fibers.

36. A process for dyeing keratin fibers according to claim 35, wherein said keratin fibers are human hair.

37. A process for dyeing keratin fibers according to claim 35, wherein said ready-to-use dye composition is left on said keratin fibers for a time ranging from 3 to 40 minutes, and then is rinsed, optionally washed with shampoo, rinsed again and dried.

38. A process for dyeing keratin fibers according to claim 37, wherein said ready-to-use dye composition is left on said keratin fibers for a time ranging from 5 to 30 minutes.

39. A process for dyeing keratin fibers comprising:
  applying at least one ready-to-use dye composition according to claim 1 to said keratin fibers, and further comprising the preliminary steps of:
  preparing a composition (A) comprising, in a medium which is suitable for dyeing, at least one oxidation base according to claim 1, at least one coupler according to claim 1, and at least one cationic direct dye according to claim 1,
  separately preparing a composition (B) comprising, in a medium which is suitable for dyeing, at least one oxidizing agent according to claim 1,
  separately storing composition (A) from composition (B), and
  mixing said composition (A) and said composition (B) together immediately before applying to said keratin fibers.

40. A process for dyeing keratin fibers comprising applying at least one ready-to-use dye composition according to claim 1 to said keratin fibers, and further comprising the preliminary steps of:
  preparing a composition (A) comprising, in a medium which is suitable for dyeing, at least one oxidation base according to claim 1 and at least one coupler according to claim 1,
  separately preparing a composition (A') comprising, in a medium which is suitable for dyeing, at least one cationic direct dye according to claim 1,
  separately preparing a composition (B) comprising, in a medium which is suitable for dyeing, at least one oxidizing agent according to claim 1, and
  mixing said composition (A), said composition (A'), and said composition (B) together immediately before applying to said keratin fibers.

41. A process according to claim 40, wherein said composition (A') is in powder form.

42. A multi-compartment dyeing kit or device, wherein said multi-compartment dyeing kit or device comprises a first compartment containing a composition (A) comprising, in a medium which is suitable for dyeing, at least one oxidation base according to claim 1, at least one coupler according to claim 1, and at least one cationic direct dye according to claim 1, and a second compartment containing an oxidizing composition (B) comprising, in a medium which is suitable for dyeing, at least one oxidizing agent according to claim 1.

43. A multi-compartment dyeing kit or device, wherein said multi-compartment dyeing "kit" or device comprises a first compartment containing a composition (A) comprising, in a medium which is suitable for dyeing, at least one oxidation base according to claim 1 and at least one coupler according to claim 1, a second compartment containing a composition (A') comprising, in a medium which is suitable for dyeing, at least one cationic direct dye according to claim 1, and a third compartment containing an oxidizing composition (B) comprising, in a medium which is suitable for dyeing, at least one oxidizing agent according to claim 1.

* * * * *